United States Patent
Yu et al.

(10) Patent No.: US 10,245,333 B2
(45) Date of Patent: Apr. 2, 2019

(54) PLASMA GENERATING APPARATUS AND TREATMENT METHOD USING THE SAME

(71) Applicant: ELECTRONICS AND TELECOMMUNICATIONS RESEARCH INSTITUTE, Daejeon (KR)

(72) Inventors: Han Young Yu, Daejeon (KR); Yark Yeon Kim, Daejeon (KR); Won Ick Jang, Daejeon (KR); Yong Sun Yoon, Daejeon (KR); Bong Kuk Lee, Daejeon (KR)

(73) Assignee: ELECTRONICS AND TELECOMMUNICATIONS RESEARCH INSTITUTE, Daejeon (KR)

(*) Notice: Subject to any disclaimer, the term of this patent is extended or adjusted under 35 U.S.C. 154(b) by 210 days.

(21) Appl. No.: 15/241,796

(22) Filed: Aug. 19, 2016

(65) Prior Publication Data
US 2017/0049913 A1 Feb. 23, 2017

(30) Foreign Application Priority Data

Aug. 19, 2015 (KR) .................. 10-2015-0116802
Jan. 12, 2016 (KR) .................. 10-2016-0003727

(51) Int. Cl.
*A61L 2/00* (2006.01)
*A61N 1/44* (2006.01)
*A61L 2/14* (2006.01)

(52) U.S. Cl.
CPC .............. *A61L 2/0011* (2013.01); *A61N 1/44* (2013.01); *A61L 2202/11* (2013.01)

(58) Field of Classification Search
CPC ............ A61L 2/0011; A61L 2/14; A61N 1/44
See application file for complete search history.

(56) References Cited

U.S. PATENT DOCUMENTS

| | | | | |
|---|---|---|---|---|
| 5,935,339 | A | * 8/1999 | Henderson | ............. G01Q 30/20 134/1 |
| 2015/0245458 | A1 | 8/2015 | Yu et al. | |
| 2015/0273231 | A1 | 10/2015 | Kim et al. | |
| 2016/0113700 | A1 | 4/2016 | Hancock et al. | |

FOREIGN PATENT DOCUMENTS

| | | |
|---|---|---|
| JP | 2007-080769 A | 3/2007 |
| JP | 2012-200459 A | 10/2012 |
| KR | 20-0166394 | 2/2000 |
| WO | WO 2014/184544 A1 | 11/2014 |

* cited by examiner

*Primary Examiner* — Kevin Joyner

(57) ABSTRACT

A plasma generating apparatus according to embodiments of the inventive concept, which provides plasma to a biological material, includes a housing configured to provide an inner space in which plasma is generated, a ground electrode coupled to one side of the housing, a power electrode coupled to the other side of the housing, and a controller configured to control a generation mode of the plasma. The generation mode includes a first mode in which the plasma is provided to the biological material while generating the plasma and a second mode in which the plasma is generated in the housing, and then the generated plasma is provided to the biological material.

18 Claims, 21 Drawing Sheets

PLASMA GENERATING APPARATUS AND TREATMENT METHOD USING THE SAME

CROSS-REFERENCE TO RELATED APPLICATIONS

This U.S. non-provisional patent application claims priority under 35 U.S.C. § 119 of Korean Patent Application Nos. 10-2015-0116802, filed on Aug. 19, 2015, and 10-2016-0003727, filed on Jan. 12, 2016, the entire contents of which are hereby incorporated by reference.

BACKGROUND

The present disclosure herein relates to a plasma generating apparatus and a treatment method using the same.

Medical application of low temperature atmospheric plasma has been progressed by using thermal characteristics of plasma for blood coagulation or tissue removal during procedure until early 2000s. From early 2000s, the low temperature atmospheric plasma has been widely applied to devices such as a harmful gas filter and an air cleaner using microorganism sterilization and disinfection characteristics of the plasma. In recent years, medical application of low temperature atmospheric plasma has been interested as a new medical device based on a research result on interaction of the plasma and a bio-cell.

To utilize the low temperature atmospheric plasma system for skin care or as a medical device, stability to temperature and also various structures according to application regions are basically required. Recent research and development regarding the plasma system is classified in two categories. First is an indirect type plasma system in which plasma is generated in a plasma generator to irradiate plasma flume to a position to be treated or managed. However, its treatment effect is slightly low. Second is a direct type plasma system in which a target to be treated or managed is utilized as a ground electrode, which has a high treatment effect. However, a target to be irradiated or treated and a power electrode almost contact each other and it has a low uniformity. Thus, a system capable of simultaneously using the direct method and the indirect method is required to effectively use the plasma on a further wider area.

SUMMARY

The present disclosure herein provides a plasma generating apparatus capable of performing direct type plasma supply and indirect type plasma supply.

The object of the present invention is not limited to the aforesaid, but other objects not described herein will be clearly understood by those skilled in the art from descriptions below.

An embodiment of the inventive concept provides a plasma generating apparatus including a housing configured to provide an inner space in which plasma is generated, a ground electrode coupled to one side of the housing, a power electrode coupled to the other side of the housing, and a controller configured to control a generation mode of the plasma. The generation mode includes a first mode in which the plasma is provided to a target to be processed while generating the plasma and a second mode in which the plasma is generated in the housing, and then the generated plasma is provided to the target to be processed.

In an embodiment, in the first mode, an electric field formed between the power electrode and the target to be processed may be greater than that formed between the power electrode and the ground electrode, and in the second mode, the electric field formed between the power electrode and the target to be processed may be less than that formed between the power electrode and the ground electrode.

In an embodiment, the plasma generating apparatus may further include an adjusting device configured to adjust a distance between the ground electrode and the power electrode, and the controller may control the adjusting device.

In an embodiment, the controller may control the adjusting device to be positioned between a first position at which a first distance between the power electrode and the target to be processed is less than a second distance between the power electrode and the ground electrode and a second position at which the first distance is greater than the second distance.

In an embodiment, the housing may include an injection port through which a process gas for generating the plasma is injected into the space and a discharge port through which the plasma is discharged from the space. The injection port, the ground electrode, the power electrode, and the discharge port may be arranged in a first direction.

In an embodiment, in a cross-section extending in the first direction of the housing, the ground electrode may be disposed so that a distance between the ground electrode and the power electrode increases as the ground electrode is away from a surface of the housing.

In an embodiment, the plasma generating apparatus may further include an ozone removing part configured to remove ozone generated when the plasma is generated.

In an embodiment, the ozone removing part may include a chamber configured to provide a collection space in which the ozone is collected, a fan disposed on one side of the chamber to form an inside of the collection space at a low pressure, and a filter configured to filter the collected ozone.

In an embodiment, one portion of the housing, which is disposed adjacent to the injection port, may have a first width, and another portion of the housing, which is disposed adjacent to the discharge port, may have a second width greater than the first width.

In an embodiment, the second width may be continuously widened from the first width in the first direction.

In an embodiment, the second width may be discontinuously widened from the first width in the first direction.

In an embodiment, the plasma generating apparatus may further include a window disposed on a surface of the housing.

In an embodiment, at least one of the ground electrode and the power electrode may include an insulator.

In an embodiment of the inventive concept, a treatment method includes injecting a process gas into a plasma generating apparatus including a power electrode and a ground electrode, generating plasma by using the process gas, and providing the plasma to a biological material to treat the biological material. The generating of the plasma to provide the plasma to the biological material includes providing the plasma to the biological material while generating the plasma when an electric field formed between the power electrode and the biological material is greater than that formed between the power electrode and the ground electrode, and generating the plasma in the housing and then providing the generated plasma to the biological material when an electric field formed between the power electrode and the biological material is less than that formed between the power electrode and the ground electrode.

In an embodiment, the treatment method may further include removing ozone generated when the plasma is generated.

In an embodiment, the removing of the ozone may include forming a low pressure region to collect the ozone when the plasma is provided, and filtering the collected ozone.

In an embodiment of the inventive concept, a plasma generating apparatus includes a housing configured to provide an inner space in which plasma is generated, a ground electrode coupled to one side of the housing, a power electrode coupled to the other side of the housing, an adjusting device configured to adjust a distance between the ground electrode and the power electrode, and a controller configured to control the adjusting device. The controller controls the adjusting device to be positioned between a first position at which a first distance between the power electrode and a target to be processed is less than a second distance between the power electrode and the ground electrode and a second position at which the first distance is greater than the second distance.

In an embodiment, the housing may include an injection port through which a process gas for generating the plasma is injected into the space and a discharge port through which the plasma is discharged from the space, and the ground electrode may be disposed between the injection port and the power electrode.

In an embodiment, the plasma generating apparatus may further include an ozone removing part configured to remove ozone generated when the plasma is generated.

In an embodiment, the ozone removing part may include a chamber configured to provide a collection space in which the ozone is collected, a fan disposed on one side of the chamber to form an inside of the collection space at a low pressure, and a filter configured to filter the collected ozone.

In an embodiment, one portion of the housing, which is disposed adjacent to the injection port, may have a first width, and another portion of the housing, which is disposed adjacent to the discharge port, may have a second width greater than the first width.

In an embodiment, the plasma generating apparatus may further include a window disposed on a surface of the housing.

Particularities of other embodiments are included in the detailed description and drawings.

BRIEF DESCRIPTION OF THE FIGURES

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings.

DETAILED DESCRIPTION

Figure 1A:
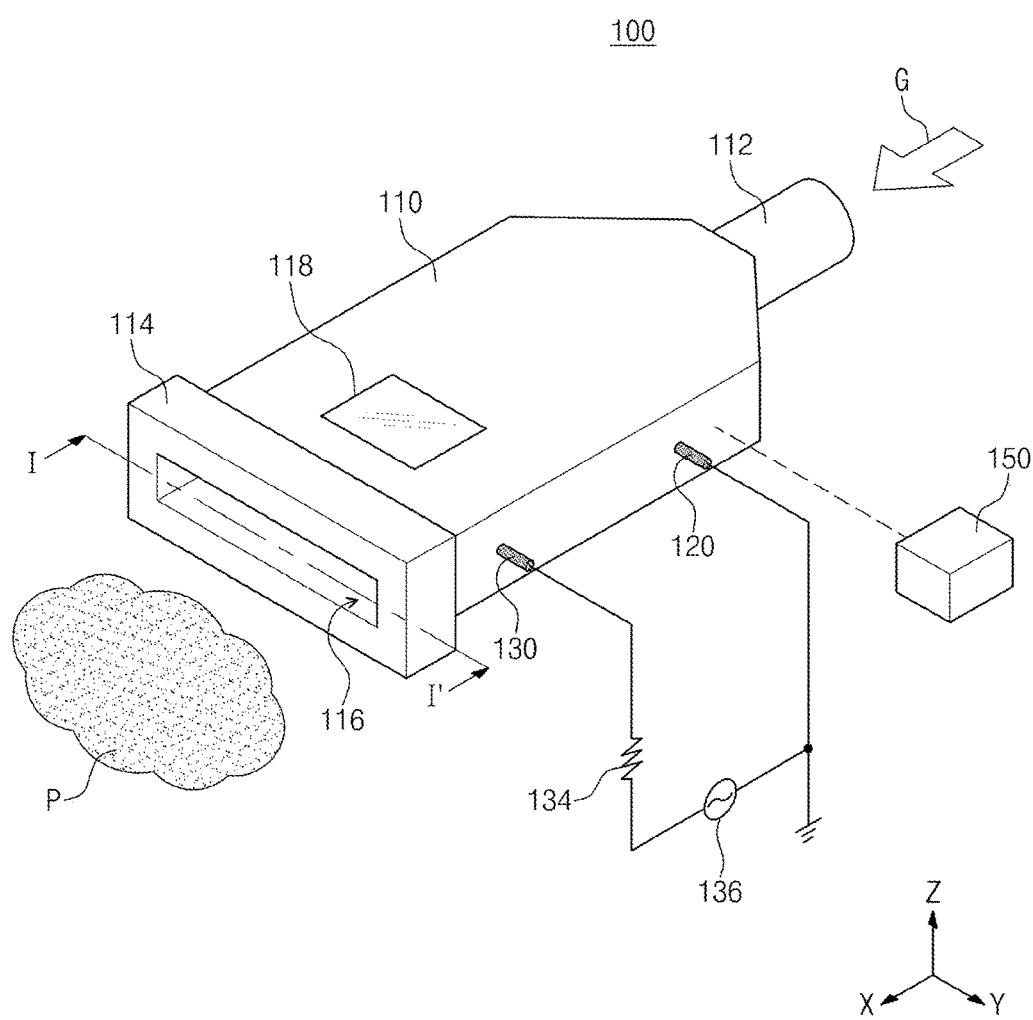
FIG. 1A is a schematic view illustrating a plasma generating apparatus according to an embodiment of the inventive concept.

Advantages and features of the present invention, and implementation methods thereof will be clarified through following embodiments described in detail with reference to the accompanying drawings. The present invention may, however, be embodied in many different forms and should not be construed as being limited to the embodiments set forth herein. Rather, these embodiments are provided so that this disclosure will be thorough and complete, and will fully convey the concept of the invention to those skilled in the art. Further, the present invention is only defined by scopes of claims. Like reference numerals refer to like elements throughout.

In the following description, the technical terms are used only for explaining a specific exemplary embodiment while not limiting the present disclosure. The terms of a singular form may include plural forms unless referred to the contrary. The meaning of "include," "comprise," "including," or "comprising," specifies a property, a region, a fixed number, a step, a process, an element and/or a component but does not exclude other properties, regions, fixed numbers, steps, processes, elements and/or components.

Additionally, the embodiment in the detailed description will be described with sectional views as ideal exemplary views of the present invention. Also, in the figures, the dimensions of layers and regions are exaggerated for clarity of illustration. Accordingly, shapes of the exemplary views may be modified according to manufacturing techniques and/or allowable errors. Therefore, the embodiments of the present invention are not limited to the specific shape illustrated in the exemplary views, but may include other shapes that may be created according to manufacturing processes. Areas exemplified in the drawings have general properties, and are used to illustrate a specific shape of a semiconductor package region. Thus, this should not be construed as limited to the scope of the present invention.

Figure 1B:
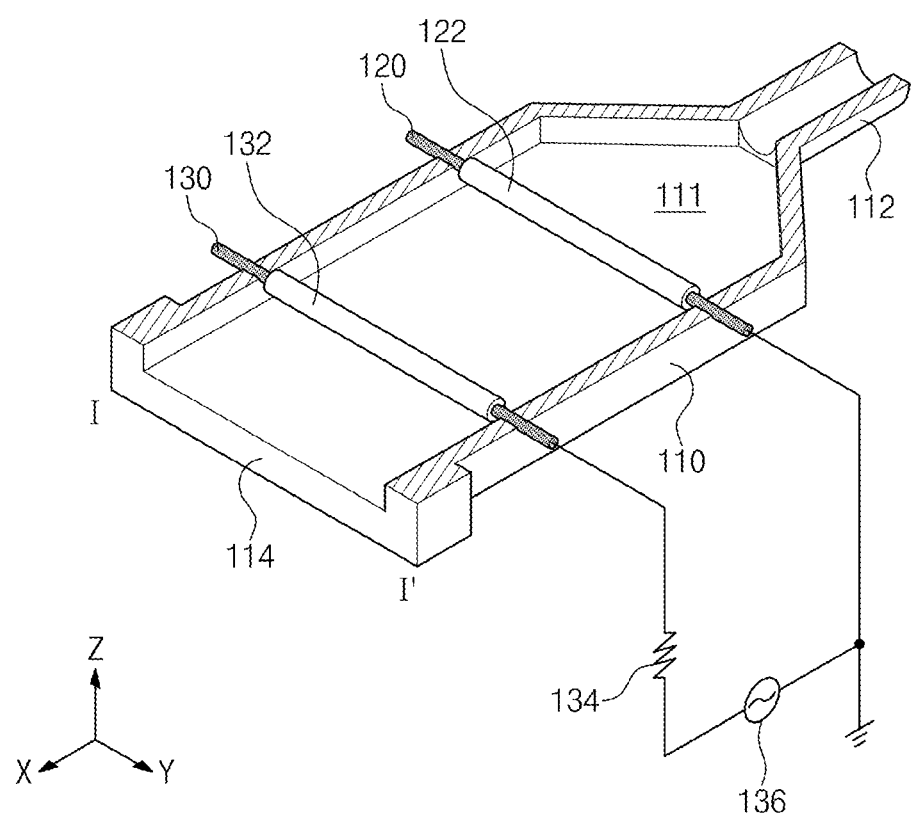
FIG. 1B is a cross-sectional view taken along line I-I' of the plasma generating apparatus of FIG. 1A.

FIG. 1A is a schematic view of a plasma generating apparatus 100 according to an embodiment of the inventive concept. FIG. 1B is a cross-sectional view taken along line I-I' of the plasma generating apparatus 100 of FIG. 1A. The plasma generating apparatus 100 includes a housing 110, a ground electrode 120, a power electrode 130, and a controller 150. The plasma generating apparatus 100 may provide plasma P to a target to be processed. For example, the target to be processed may include a biological material. The plasma generating apparatus 100 may generate the plasma P to provide the plasma P to a biological material (refer to 200 in FIG. 2A) and treat the biological material 200. For example, the plasma generating apparatus 100 may be provided as a nozzle.

The housing 110 may have a tube shape. The housing 110 provides an inner space 111 in which the plasma P is generated. The housing 110 may include an injection port 112, a discharge port 114, and a window 118. Hereinafter, a direction heading from the injection port 112 to the discharge port 114 is defined as a first direction X, a direction perpendicular to the first direction X is defined as a second direction Y, and a direction perpendicular to the first direction X and the second direction Y is defined as a third direction Z. Through the injection port 112, a process gas G may be provided into the inner space 111. The process gas G may include a discharge gas and a carrier gas. The plasma P generated in the inner space 111 is discharged through the discharge port 114. According to a shape of the housing 110, a shape of a plasma discharge passage 116 may be determined, and a shape of a plasma plume generated may be varied according to the shape of the plasma discharge passage 116. For example, a length and a width of the plasma plume P may be varied. Hereinafter, the plasma plume is referred to as the plasma P. The inner space 111 of the housing 110 may be monitored through the window 118. Whether the plasma P is generated or not may be checked through the window 118. For example, when the window 118 includes the power electrode 130, whether the plasma P is generated by a first mode and a second mode or not may be checked according to density difference of the plasma on the basis of a position.

Along the first direction X, the injection port 112, the ground electrode 120, the power electrode 130, and the discharge port 114 may be sequentially provided. The ground electrode 120 and the power electrode 130 may be provided in parallel to each other. The ground electrode 120 may be coupled to one side of the housing 110. For example, as illustrated in FIGS. 1A and 1B, the ground electrode 120 may be provided in the housing 110 to pass through the side surface of the housing 110. The ground electrode 120 may include a first insulator 122 surrounding the ground electrode 120. The power electrode 130 may be connected to a plasma power 136. The plasma power 136 may include alternating current, bipolar pulse, unipolar pulse, or direct current DC passing through a capacitor. The power electrode 130 may include a second insulator 132 surrounding the power electrode 130. The power electrode 130 and the ground electrode 120 may be connected to a resistor 134 for stability of the plasma power 136 and preventing overcurrent. As the power electrode 130 and the ground electrode 120 are surrounded by the insulators 122 and 132, arch discharge or filamentary discharge may be prevented.

The controller 150 may control a plasma generation mode. Hereinafter, referring to FIGS. 2A and 2B, the plasma generation modes will be described.

Figure 2A:
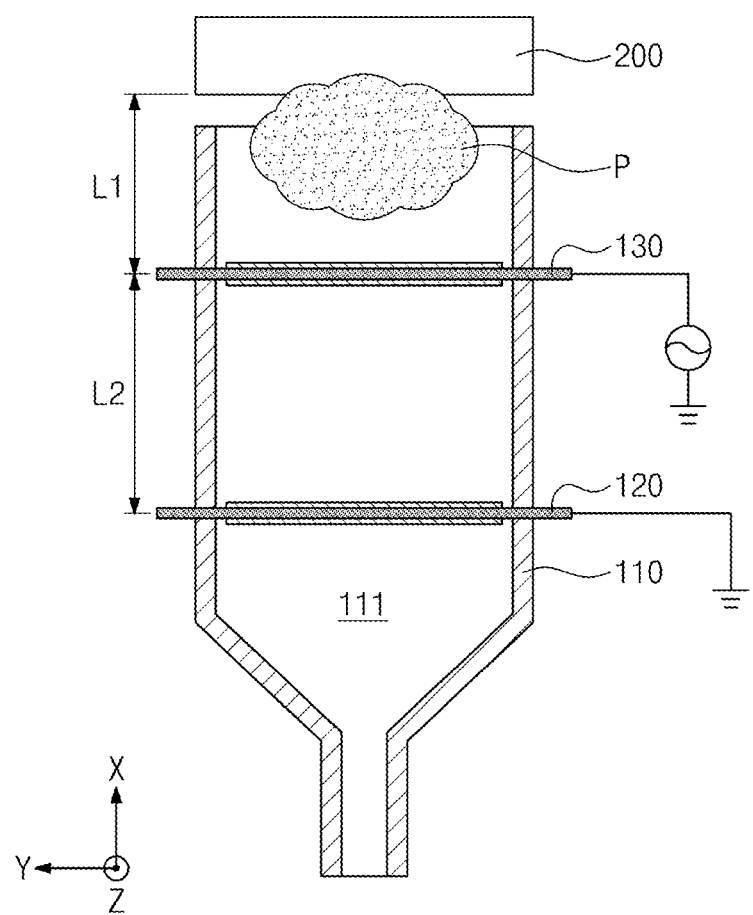
FIG. 2A is a view illustrating plasma generated in a first mode.
Figure 2B:
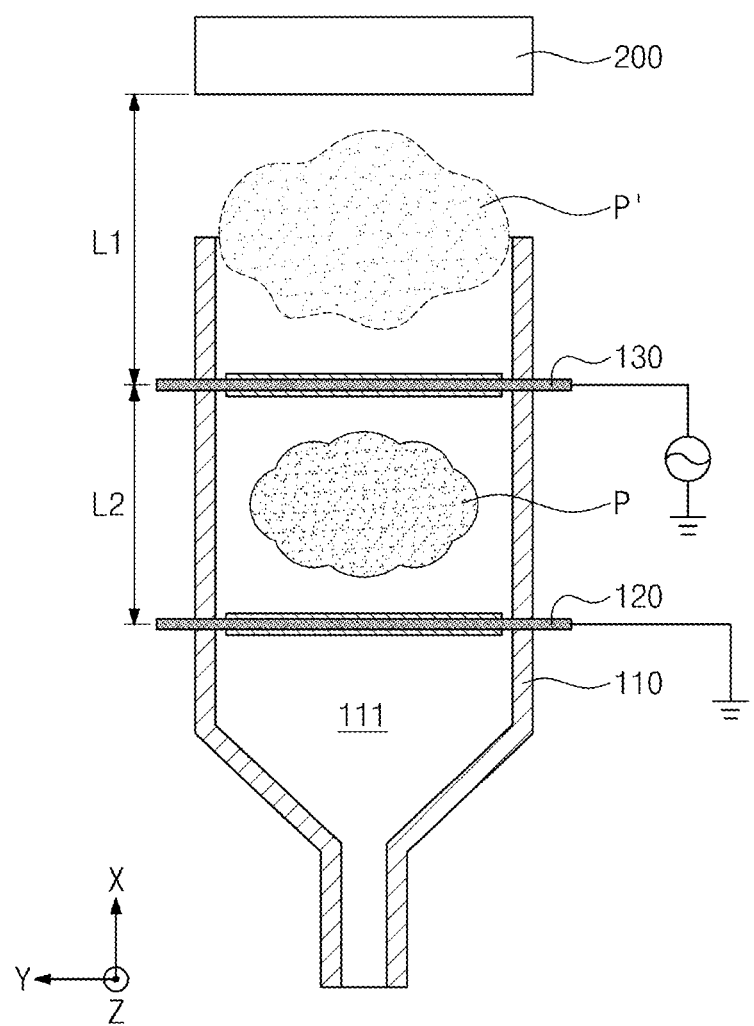
FIG. 2B is a view illustrating plasma generated in a second mode.

FIG. 2A is a view illustrating that the plasma generating apparatus 100 generates the plasma P in a first mode, and FIG. 2B is a view illustrating that the plasma generating apparatus 100 generates the plasma P in a second mode. In the first mode, the plasma P is generated and simultaneously directly provided to the biological material 200. In the second mode, the plasma P is generated in the plasma generating apparatus 100, and then the pre-generated plasma is provided to the biological material 200. For example, the pre-generated plasma may be provided to the biological material 200 by the carrier gas. In the first mode, high effects of treatment and cure may be provided because the plasma P provided to the biological material 200 has a high density. In the second mode, a risk caused by malfunction of the plasma apparatus may be minimized.

The first and second modes may be determined according to intensities of electric fields formed between the power electrode 130 and the biological material 200 and between the power electrode 130 and the ground electrode 120. For example, the first mode may include a case in which the electric field formed between the power electrode 130 and the biological material 200 is greater in intensity than electric field formed between the power electrode 130 and the ground electrode 120, and the second mode may include a case in which the electric field formed between the power electrode 130 and the biological material 200 is less in intensity than electric field formed between the power electrode 130 and the ground electrode 120. In the first mode, the biological material 200 may have the same effect as that of the ground electrode. In more detail, pre-ionization may be generated between the power electrode 130 and the ground electrode 120, and the plasma P may be generated by the electric field formed between the power electrode 130 and the biological material 200.

When the same voltage is applied to the power electrode 130 and the power electrode 130 and the ground electrode 120 have the same insulator condition, and like FIG. 2A, when a first distance L1 between the power electrode and the biological material is closer than a second distance L2 between the power electrode and the ground electrode, the controller 150 may spray the plasma P in the first mode. Meanwhile, like FIG. 2B, when the first distance L1 between the power electrode and the biological material is further than the second distance L2 between the power electrode and the ground electrode, the controller 150 may spray plasma P' in the second mode.

Figure 3A:
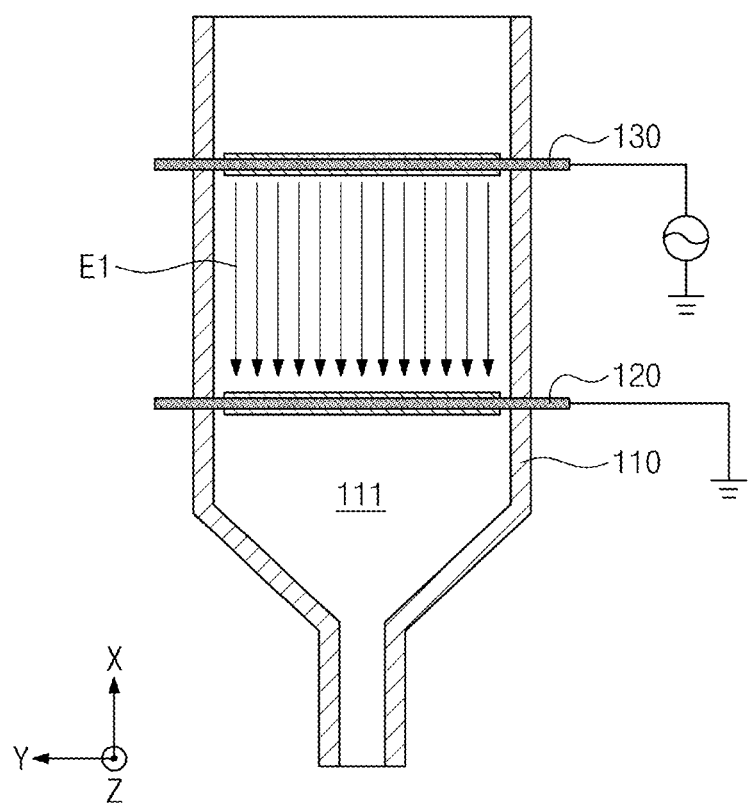
FIG. 3A is a view illustrating an electric field formed between a power electrode and a ground electrode.
Figure 3B:
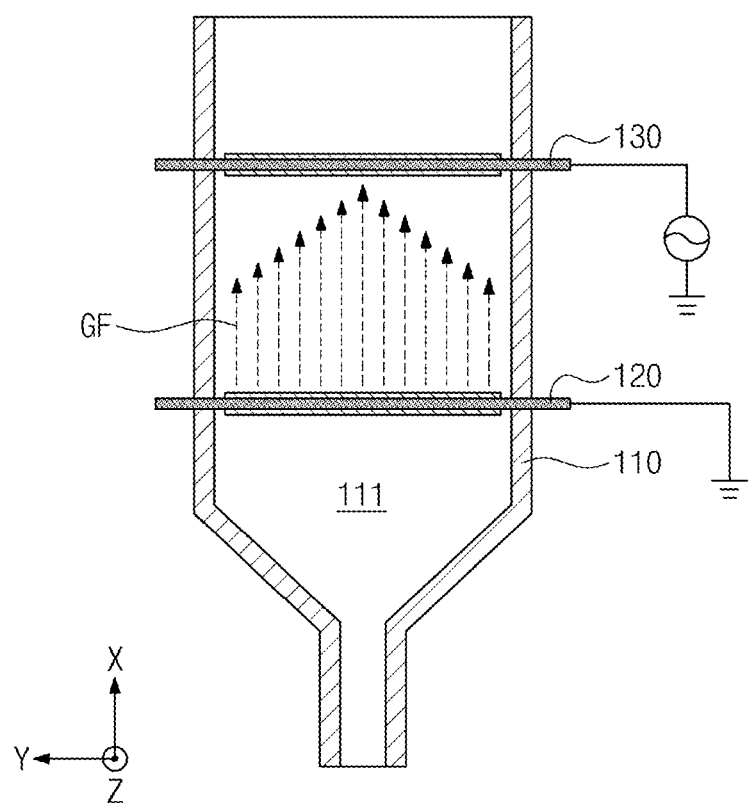
FIG. 3B is a view illustrating process gas flow formed between the power electrode and the ground electrode.

FIG. 3A is a view illustrating an electric field E1 formed between the power electrode 130 and the ground electrode 120, and FIG. 3B is a view illustrating flow GF of the process gas formed between the power electrode 130 and the ground electrode 120. While the electric field E1 may be uniformly formed between the power electrode 130 and the ground electrode 120, the flow GF of the process gas may be interfered by a surface of the housing 110. Accordingly, the flow of the process gas may be varied according to a distance from the surface of the housing 110. For example, the flow GF of the process gas may have a speed that is slow at the surface of the housing and fast at a central portion of the housing 110. The generation and dissipation of the plasma P may be influenced by the flow GF of the process gas and the electric field E1. The process gas is separated into electrons and ions by the plasma power 136 to generate the plasma P, and when the generated plasma P collides with the surrounding process gas or the surface of the housing 110, the plasma P may be varied in state to return to a steady state. Accordingly, for uniform and continuous formation of the plasma, it is effective that the flow GF of the gas and the intensity of the electric field E1 are complementary to each other.

Figure 3C:
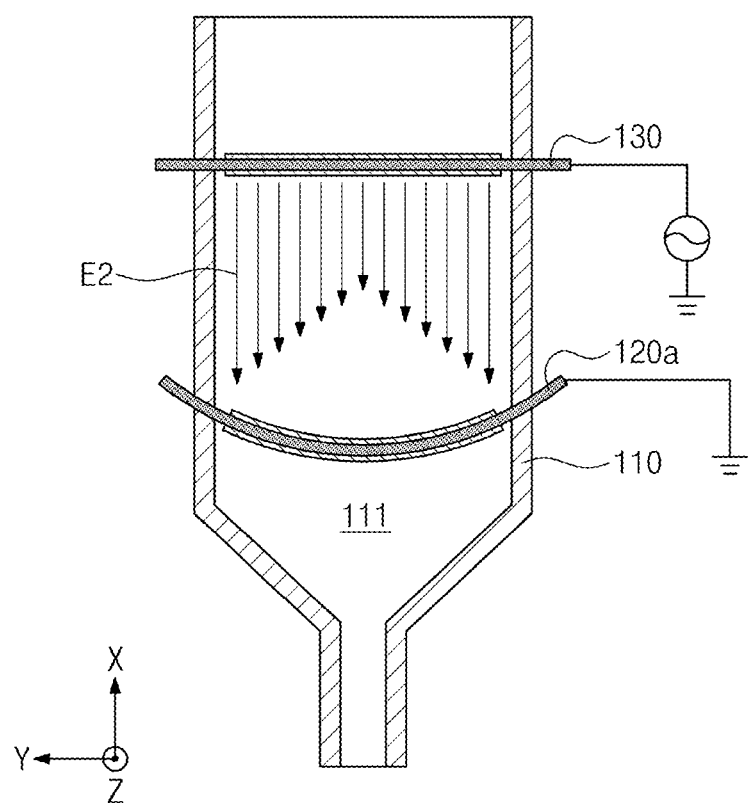
FIG. 3C is a view illustrating a plasma generating apparatus according to an embodiment of the inventive concept.

FIG. 3C is a view of a plasma generating apparatus 100a according to an embodiment of the inventive concept. Like reference numerals denote like elements of the plasma generating apparatus 100a, which are substantially the same as those of the plasma generating apparatus 100 described with reference to FIGS. 1A to 3B. For simplicity of description, duplicated description may be omitted. A ground electrode 120a of the plasma generating apparatus 100a has a cross-section extending in the first direction X so that a distance between the power electrode 130 and the ground electrode 120a increases as the ground electrode 120a is away from the surface of the housing 110.

That is, the ground electrode 120a may have an arc shape in which a portion disposed at a central portion of the housing 110 is farthest from the power electrode 130. Accordingly, an electric field E2 formed between the power electrode 130 and the ground electrode 120a may increase as the electric field E2 is adjacent to the surface of the housing 110 and decrease as the electric field E2 is adjacent to the central portion of the housing 110. Thus, the plasma generating apparatus 100a may further uniformly and continuously provide the plasma P by complimentarily designing the process gas flow (refer to GF in FIG. 3B) and the electric field E2 between the power electrode 130 and the ground electrode 120a.

Figure 4A:
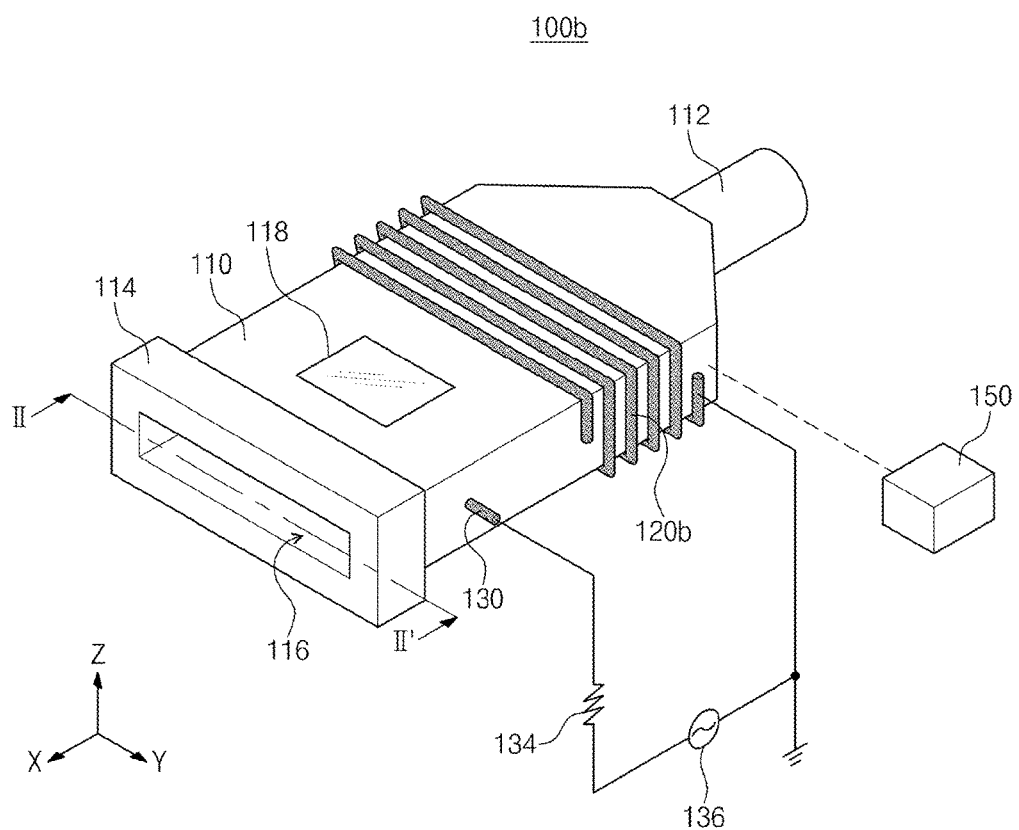
FIG. 4A is a view illustrating a plasma generating apparatus according to an embodiment of the inventive concept.
Figure 4B:
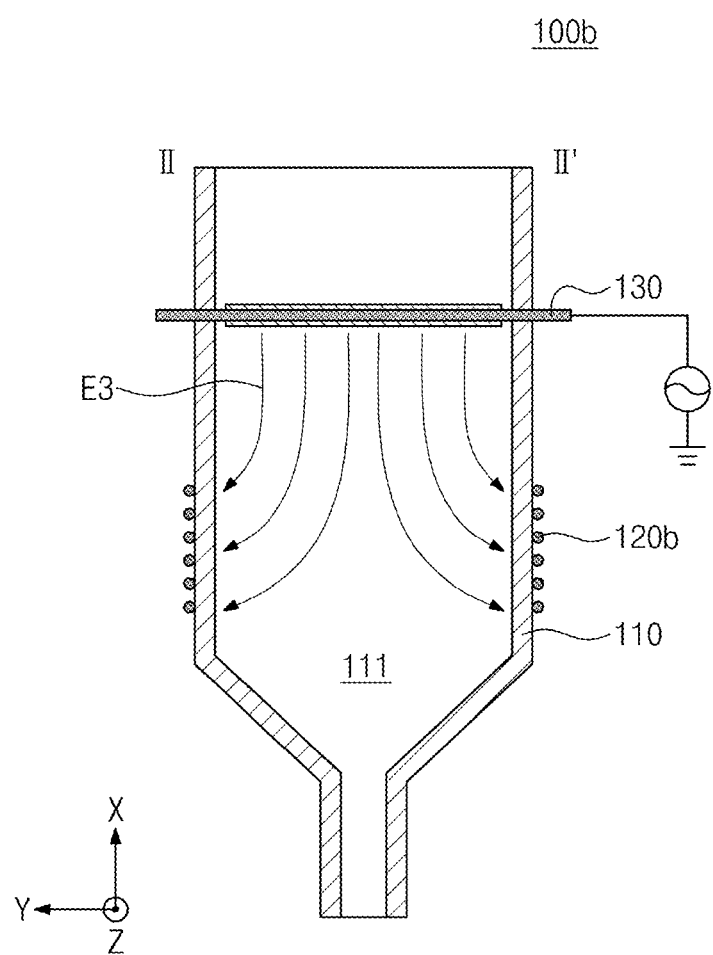
FIG. 4B is a cross-sectional view taken along line II-II' of FIG. 4A.

FIG. 4A is a view of a plasma generating apparatus 100b according to an embodiment of the inventive concept. FIG. 4B is a cross-sectional view taken along line II-II' of FIG. 4A. FIG. 4B is a view illustrating an electric field E3 formed between a ground electrode 120b and the power electrode 130. Like reference numerals denote like elements of the plasma generating apparatus 100b, which are substantially the same as those of the plasma generating apparatus 100 described with reference to FIGS. 1A to 3B. For simplicity of description, duplicated description may be omitted. The ground electrode 120b may surround an outer surface of the housing 110. For example, the ground electrode 120b may have a coil or wire shape. When the ground electrode 120b has a wire shape, each of the electric fields E3 formed from the power electrode 130 to the ground electrode 120b has a different intensity by a resistance of each of the wires. That is, the electric field between the power electrode 130 and the ground electrode disposed closest thereto have a strongest intensity, and as the ground electrode is away from the power electrode 130, the intensity of the electric field therebetween decreases. Accordingly, the electric field E3 formed between the power electrode and the ground electrode has the strongest intensity at the surface of the housing 110, and the intensity gradually decreases as the electric field E3 is adjacent to the central portion of the housing 110. Thus, the plasma generating apparatus 100b may provide the further uniform and continuous plasma P by complimentarily designing the process gas flow (refer to GF in FIG. 3B) and the electric field E3 between the power electrode 130 and the ground electrode 120b.

Figure 5:
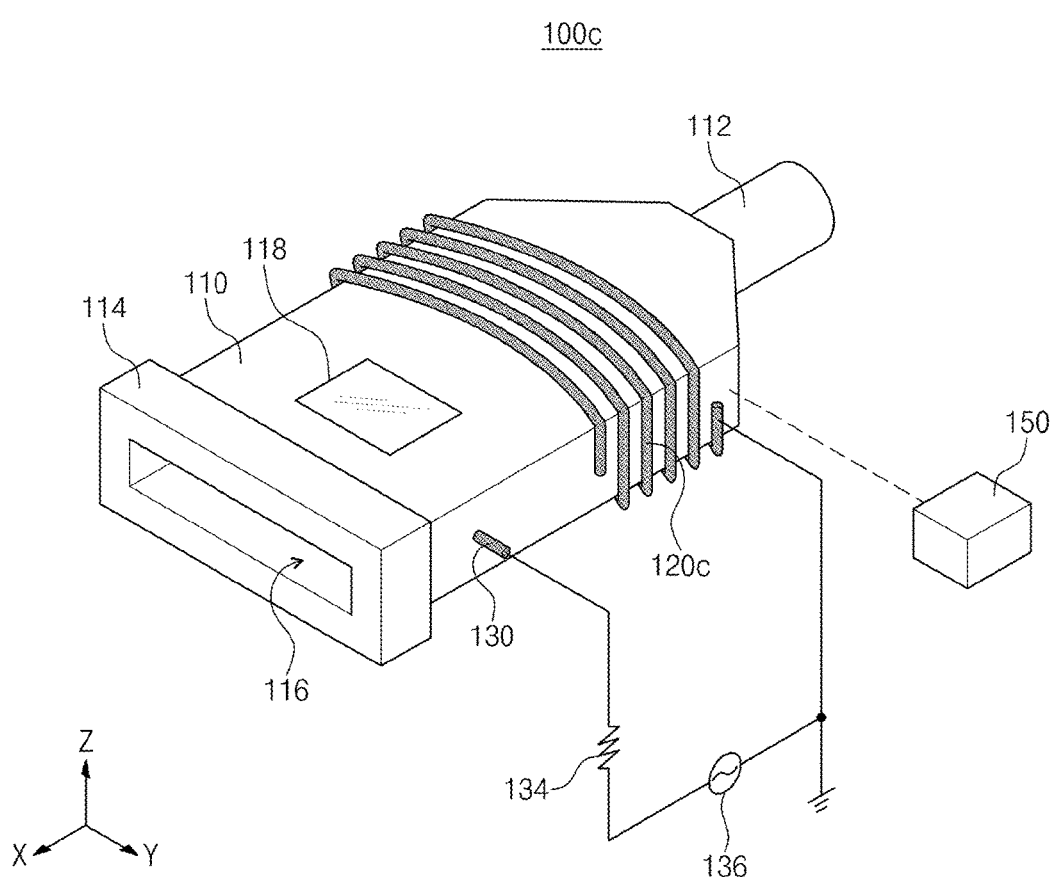
FIG. 5 is a view illustrating a plasma generating apparatus according to an embodiment of the inventive concept.

FIG. 5 is a view of a plasma generating apparatus 100c according to an embodiment of the inventive concept. Like reference numerals denote like elements of the plasma generating apparatus 100c, which are substantially the same as those of the plasma generating apparatus 100b described with reference to FIGS. 4A to 4B. For simplicity of description, duplicated description may be omitted. A distance between a ground electrode 120c and the power electrode 130 may increase as the ground electrode 120c is away from the surface of the housing 110 on a cross-section extending in the first direction X. That is, the ground electrode 120c may have an arc shape in which a portion disposed at a central portion of the housing 110 is farthest from the power electrode 130. Accordingly, the electric field formed between the power electrode 130 and the ground electrode 120c may increase as the electric field is adjacent to the surface of the housing 110 and decrease at the central portion of the housing 110. Thus, the plasma generating apparatus 100c may provide the further uniform and continuous plasma P by complimentarily designing the process gas flow (refer to GF in FIG. 3B) and the electric field E3 between the power electrode 130 and the ground electrode 120c.

Figure 6A:
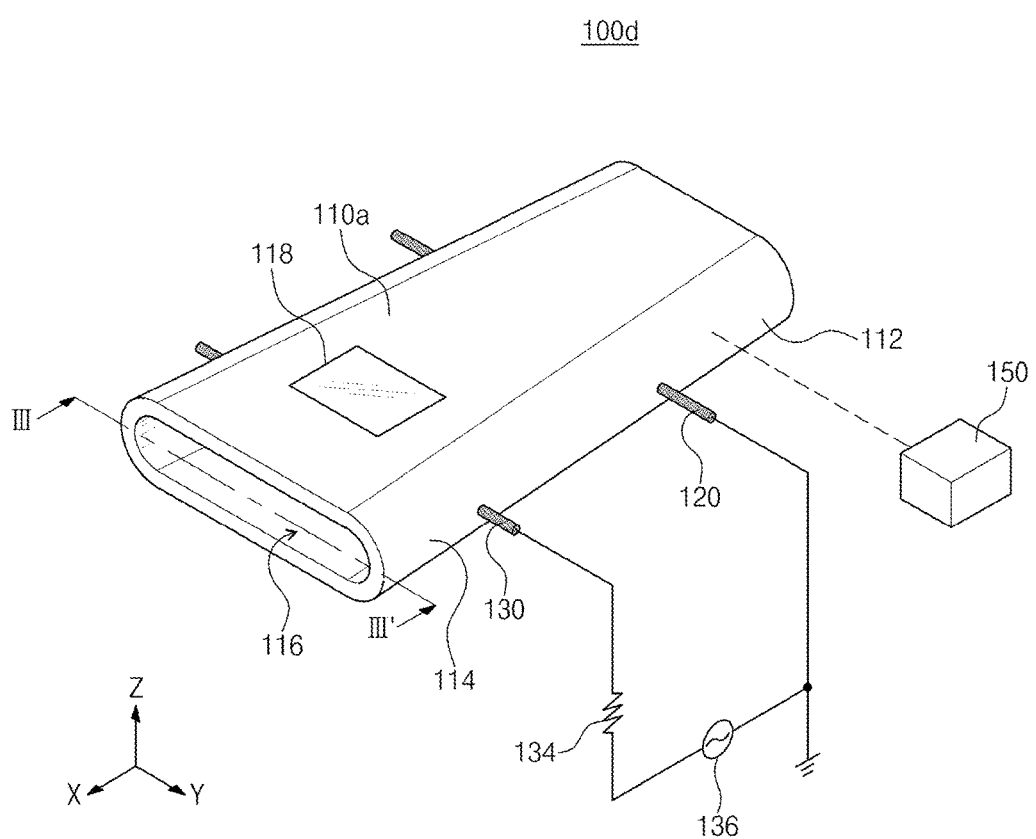
FIG. 6A is a view of a plasma generating apparatus 100d according to an embodiment of the inventive concept.
Figure 6B:
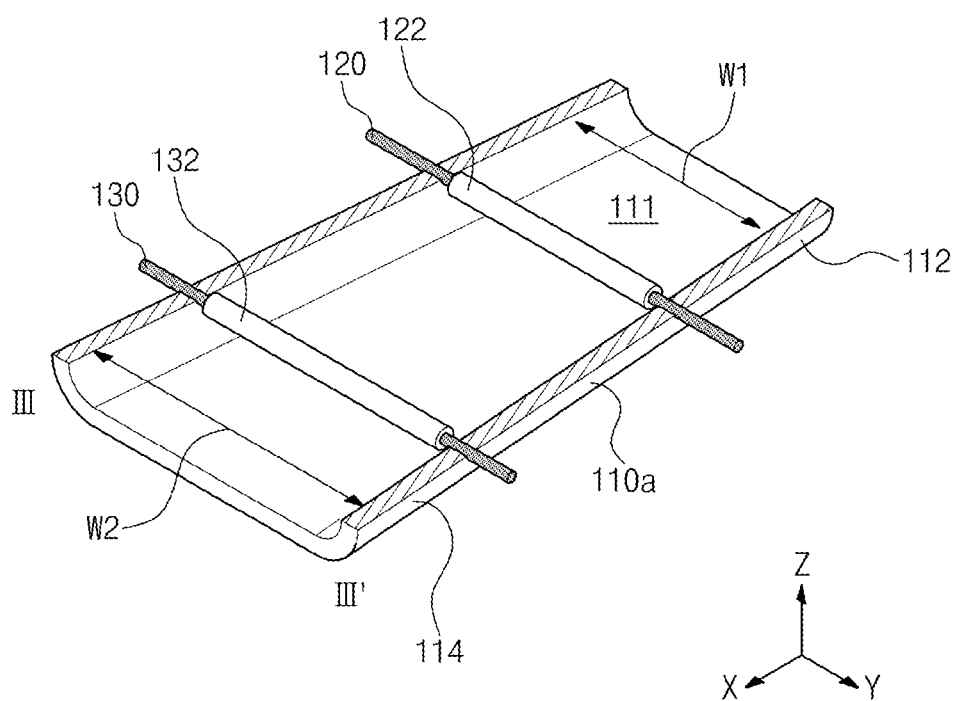
FIG. 6B is a cross-sectional view taken along line III-III' of FIG. 6A.

FIG. 6A is a view of a plasma generating apparatus 100d according to an embodiment of the inventive concept. FIG. 6B is a cross-sectional view taken along line III-III' of FIG. 6A. Like reference numerals denote like elements of the plasma generating apparatus 100d, which are substantially the same as those of the plasma generating apparatus 100 described with reference to FIGS. 1A to 3B. For simplicity of description, duplicated description may be omitted. Referring to FIGS. 6A and 6B, a housing 110a disposed adjacent to the injection port 112 may have a first width W1, and the housing 110a disposed adjacent to the discharge port 114 may have a second width W2. Here, the second width W2 may be greater than the first width W1. The width may be continuously and gradually widened from the first width W1 to the second width W2 in the first direction X. The plasma discharge passage 116 of the discharge port 114 may have a rounded edge that is processed in consideration of friction of a discharge gas. As the housing 110a expands from the injection port 112 to the discharge port 114, mutual collision in the gas for generating the plasma may be reduced to provide the large-area plasma P.

Figure 7A:
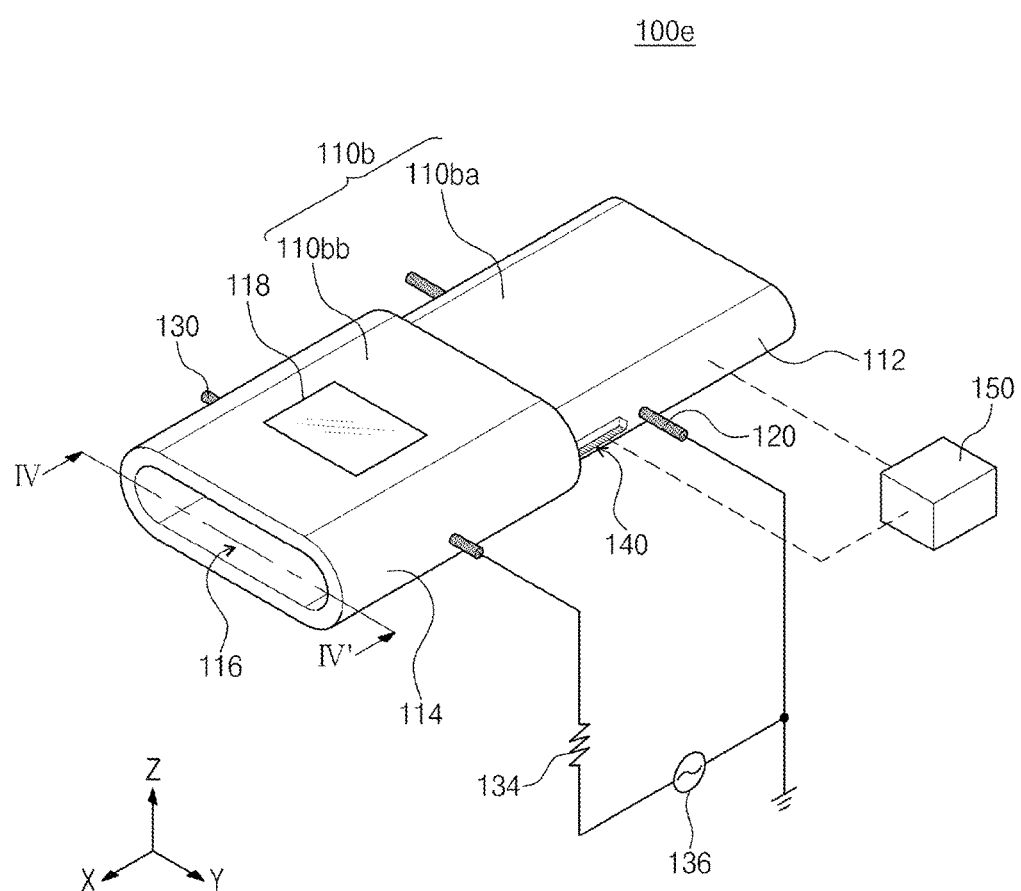
FIG. 7A is a view illustrating a plasma generating apparatus according to an embodiment of the inventive concept.
Figure 7B:
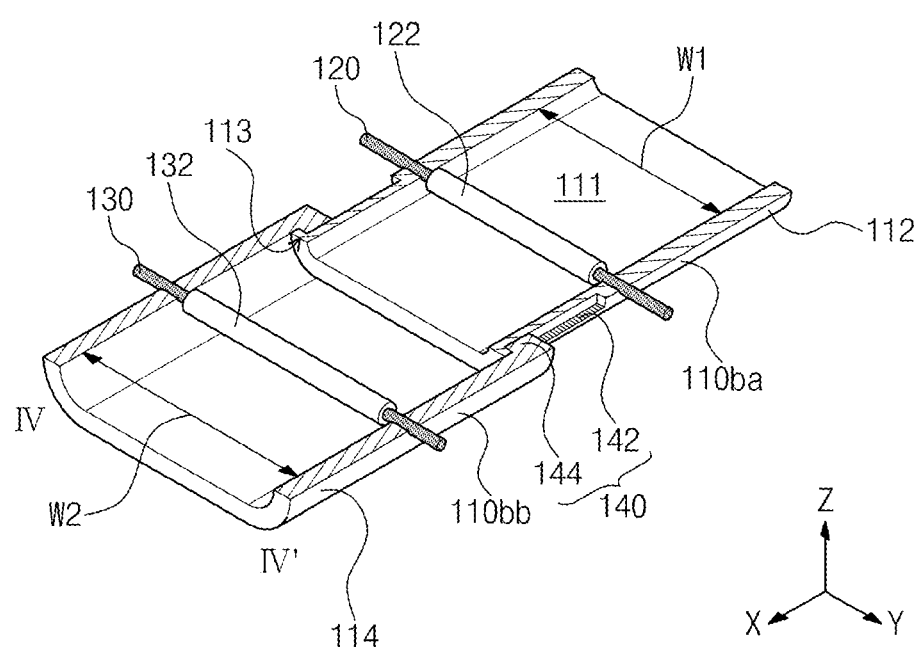
FIG. 7B is a cross-sectional view taken along line IV-IV' of FIG. 7A.

FIG. 7A is a view of a plasma generating apparatus 100e according to an embodiment of the inventive concept. FIG. 7B is a cross-sectional view taken along line IV-IV' of FIG. 7A. Like reference numerals denote like elements of the plasma generating apparatus 100e, which are substantially the same as those of the plasma generating apparatus 100d described with reference to FIGS. 6A to 6B. For simplicity of description, duplicated description may be omitted.

A housing 110b may include a first body 110ba and a second body 110bb, which are coupled to each other. For example, the first body 110ba may be inserted into the second body 110bb. Referring to FIGS. 7A and 7B, the first body 110ba disposed adjacent to the injection port 112 may have a first width W1, and the second body 110bb disposed adjacent to the discharge port 116 may have a second width W2. Here, the second width W2 may be greater than the first width W1. The width may be discontinuously widened from the first width W1 to the second width W2 in the first direction X. When each of the first body 110ba and the second body 110bb has a rectangular shape, a portion of the first body 110ba may be inserted into the second body 110bb. Here, the process gas may form a vortex in a discontinuous stepped portion 113 provided by the first body 110ba and the second body 110bb. Because of the vortex, the gas flow in the second body 110bb may be uniformly formed to maintain the uniformity of the plasma. The uniform process gas flow may further easily form the discharge of the plasma generated by the electric field. As the first body 110ba expands from the injection port 112 to the discharge port 114, mutual collision in the gas for generating the plasma may be reduced to provide the large-area plasma P.

The plasma generating apparatus 100e may further include an adjusting device 140. The adjusting device 140 may adjust a distance between the power electrode 130 and the ground electrode 120. The adjusting device 140 may include a guide 142 and a fixing part 144. For example, the adjusting device 140 may be coupled to one side of the housing 110b. The guide 142 may be coupled to the first body 110ba, and the fixing part 144 may be coupled to the second body 110bb. The fixing part 144 may move along the guide 142 to adjust a distance between the power electrode 130 and the ground electrode 120. Alternatively, the adjusting device 140 may include a motor or the like. The controller 150 may control the adjusting device 140 to control a control mode of the plasma generating apparatus 100e. For example, the controller 150 may enable the adjusting device 140 to move between a first position and a second position.

Figure 8A:
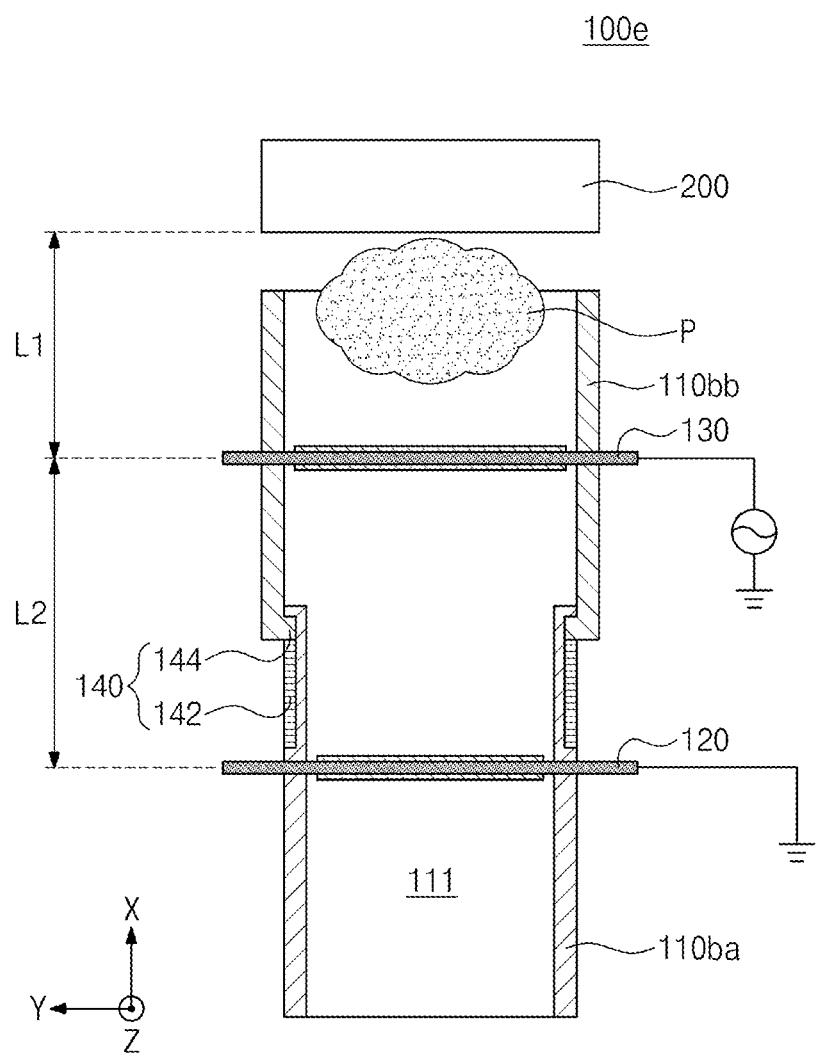
FIG. 8A is a view illustrating plasma generated in the first mode with the plasma generating apparatus of FIG. 7A.
Figure 8B:
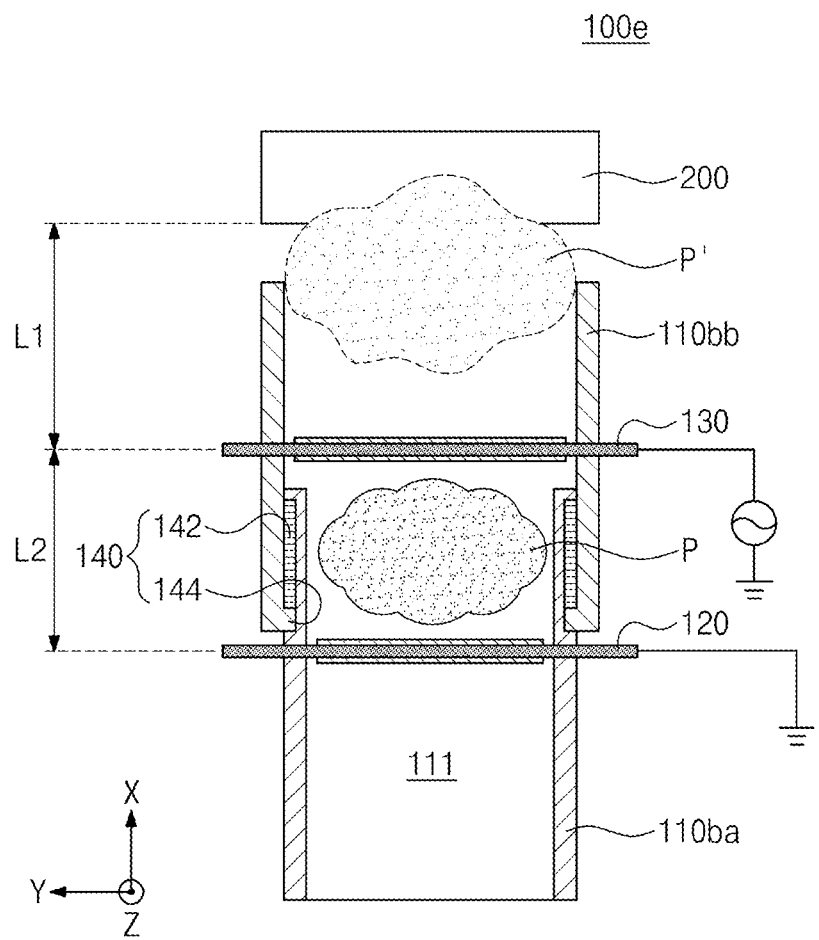
FIG. 8B is a view illustrating plasma generated in the second mode with the plasma generating apparatus of FIG. 7A.

FIG. 8A is a view illustrating that the plasma generating apparatus 100e generates the plasma P in the first mode, and FIG. 8B is a view illustrating that the plasma generating apparatus 100e generates the plasma P in the second mode.

When the controller 150 generates the plasma P in the first mode, the adjusting device 140 may be controlled to position a first distance L1 between the power electrode and the biological material to a first position so that the first distance L1 is less than a second distance L2 between the power electrode and the ground electrode. Meanwhile, when the controller 150 generates the plasma P in the second mode, the adjusting device 140 may be controlled to position the first distance L1 between the power electrode and the biological material to a second position so that the first distance L1 is greater than a second distance L2 between the power electrode and the ground electrode.

Figure 9A:
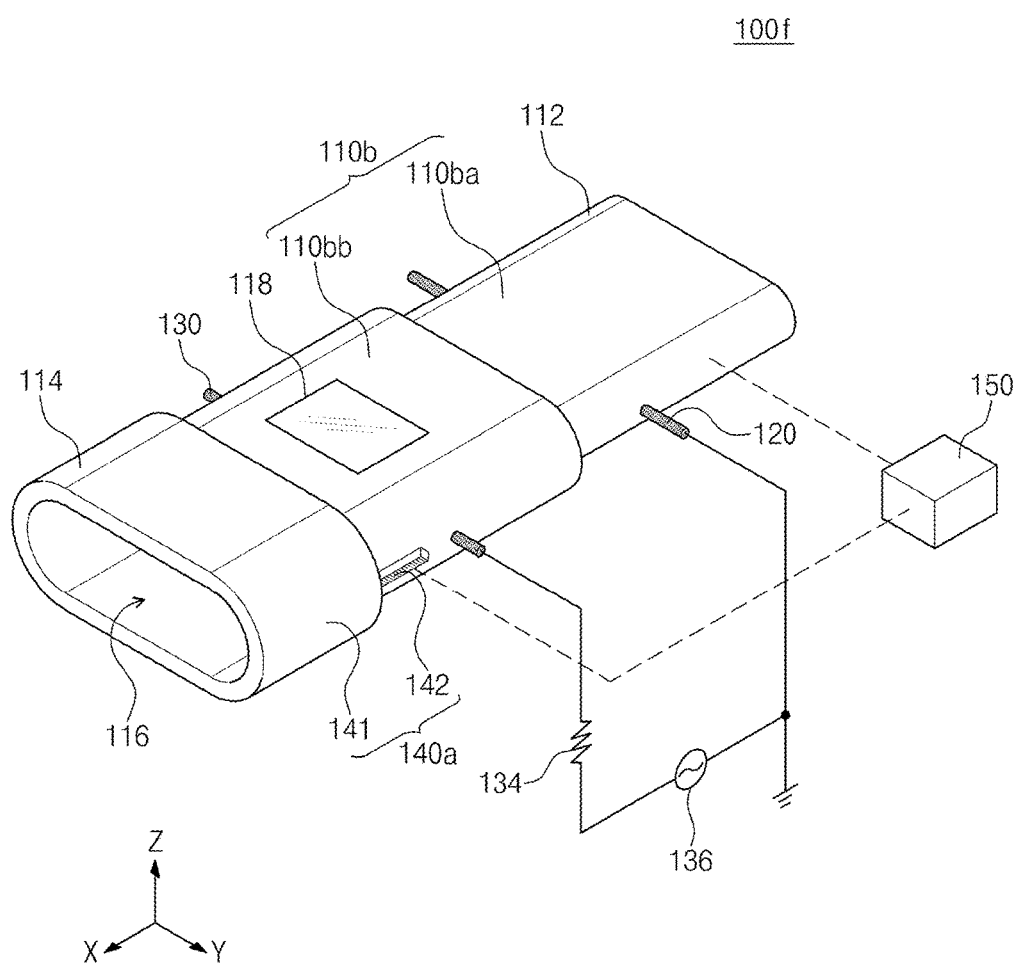
FIG. 9A is a view illustrating a plasma generating apparatus according to an embodiment of the inventive concept.
Figure 9B:
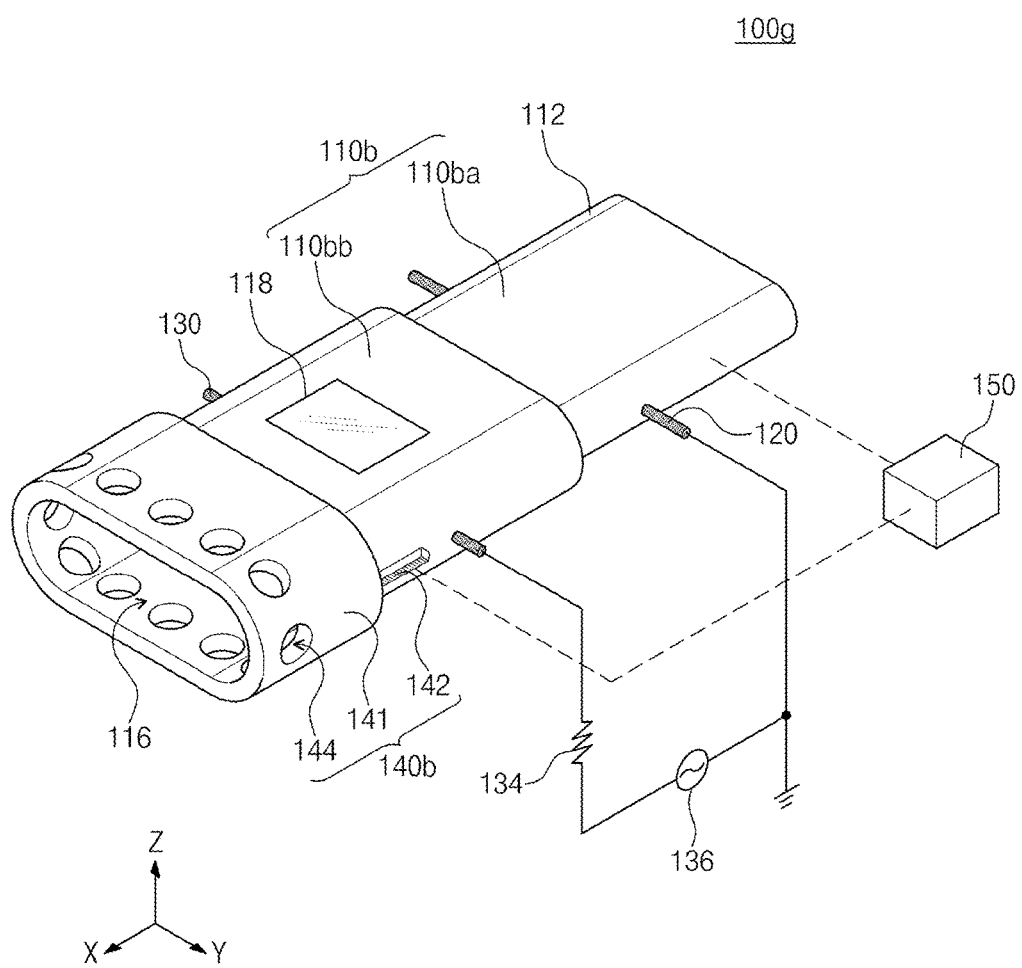
FIG. 9B is a view illustrating a plasma generating apparatus according to an embodiment of the inventive concept.

FIG. 9A is a view of a plasma generating apparatus 100f according to an embodiment of the inventive concept. FIG. 9B is a view of the plasma generating apparatus 100g according to an embodiment of the inventive concept. Like reference numerals denote like elements of the plasma generating apparatuses 100f and 100g, which are substantially the same as those of the plasma generating apparatus 100e described with reference to FIGS. 7A to 8B. For simplicity of description, duplicated description may be omitted. An adjusting device 140a of the plasma generating apparatus 100f may adjust a distance between the biological material and the plasma discharge passage 116. The adjusting device 140a may include an adjusting body 141 and a guide 142. The adjusting body 141 may be coupled to a housing 110b. For example, the adjusting body 141 may be coupled to a second body 110bb. As the controller 150 adjusts a position of the adjusting body 141 so that the adjusting body 141 moves along the guide 142, a distance between the adjusting body 141 and the biological electrode may be adjusted. An adjusting device 140b of the plasma generating apparatus 100g may further include a sub-discharge port 144. When the adjusting device 140b enables the adjusting body 141 to contact the biological material, the plasma may be discharged to the outside through the sub-discharge port 144 disposed on a side surface of the adjusting body 141. The sub-discharge port 144 may be disposed on the side surface of the adjusting body 141, and the shape and number thereof are not limited.

Although the plasma discharge passage 116 of the adjusting body 141 has a cylindrical shape in FIGS. 9A and 9B, the shape of the adjusting body 141 is not limited thereto. For example, the adjusting body 141 may have an area gradually expanding toward the plasma discharge passage 116. Although not shown, the adjusting apparatuses 140a and 140b may further include a fixing part facing the guide 142. Also, each of the plasma generating apparatuses 100f and 100g may include the housing having various shapes. When indirect type plasma is generated from the plasma generating apparatuses 100f and 100g, the controller 150 may control the adjusting devices 140a and 140b so that the housing 110b further closely approaches the biological material, thereby generating direct type plasma.

Figure 10:
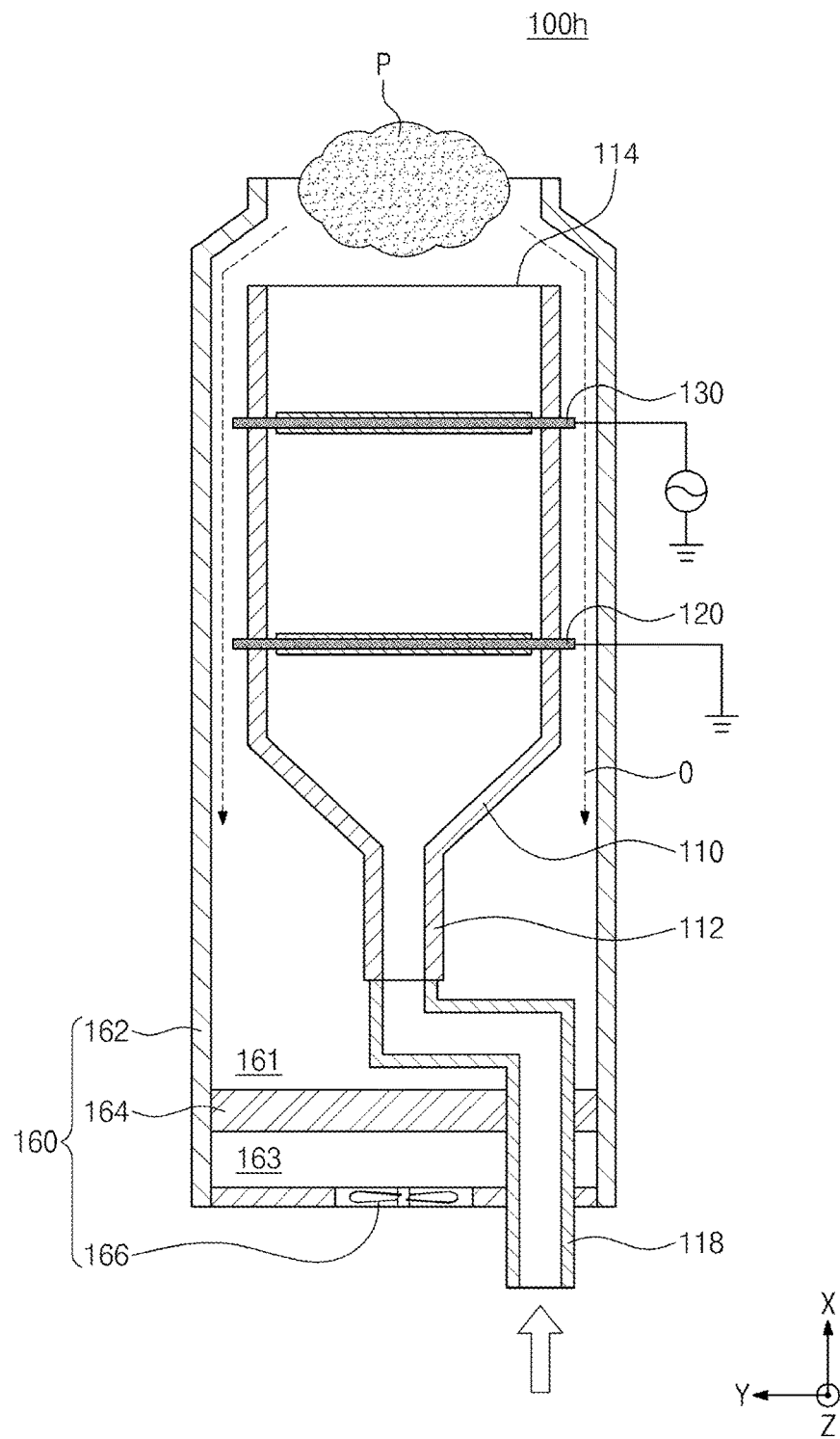
FIG. 10 is a view illustrating a plasma generating apparatus according to an embodiment of the inventive concept.

FIG. 10 is a view of a plasma generating apparatus 100h according to an embodiment of the inventive concept. Like reference numerals denote like elements of the plasma generating apparatus 100h, which are substantially the same as those of the plasma generating apparatus 100 described with reference to FIGS. 1A to 1B. For simplicity of description, duplicated description may be omitted. The plasma generating apparatus 100h may further include an ozone removing part 160. When the plasma P is formed and supplied to the biological material to perform reformation and management of the biological material, ozone (O3) may be generated. When the ozone (O3) is generated over a reference value, since it may be harmful to a human body, the plasma generating apparatus 100h may further include the ozone removing part 160.

The ozone removing part 160 may include a chamber 162, a fan 166, and a filter 164. The housing 110 may be provided in the chamber 162. For example, the chamber 162 may have a collection space 161 in which the ozone (O3) is collected, and the housing 110 may be provided in the collection space 161. The fan 166 may be provided on one side of the chamber 162. Desirably, the fan 166 may be provided on a position facing the discharge port 114 through which the plasma P is discharged. Here, a supply port 118 through which the process gas is provided to the injection port 112 may be provided on one side of the fan 166. The fan 166 may form an inside of the collection space 161 at a low pressure. Accordingly, the ozone (O3) may be easily collected into the collection space 161. The filter 164 may be provided between the collection space 161 and the fan 166. For example, the filter 164 may divide the collection space 161 to provide a first collection space 161 and a second collection space 163. The filter 164 may absorb the ozone (O3) to remove the ozone (O3). Selectively, the plasma generating apparatus 100f may further include a UV device (not shown) for removing the ozone (O3).

Figure 11:
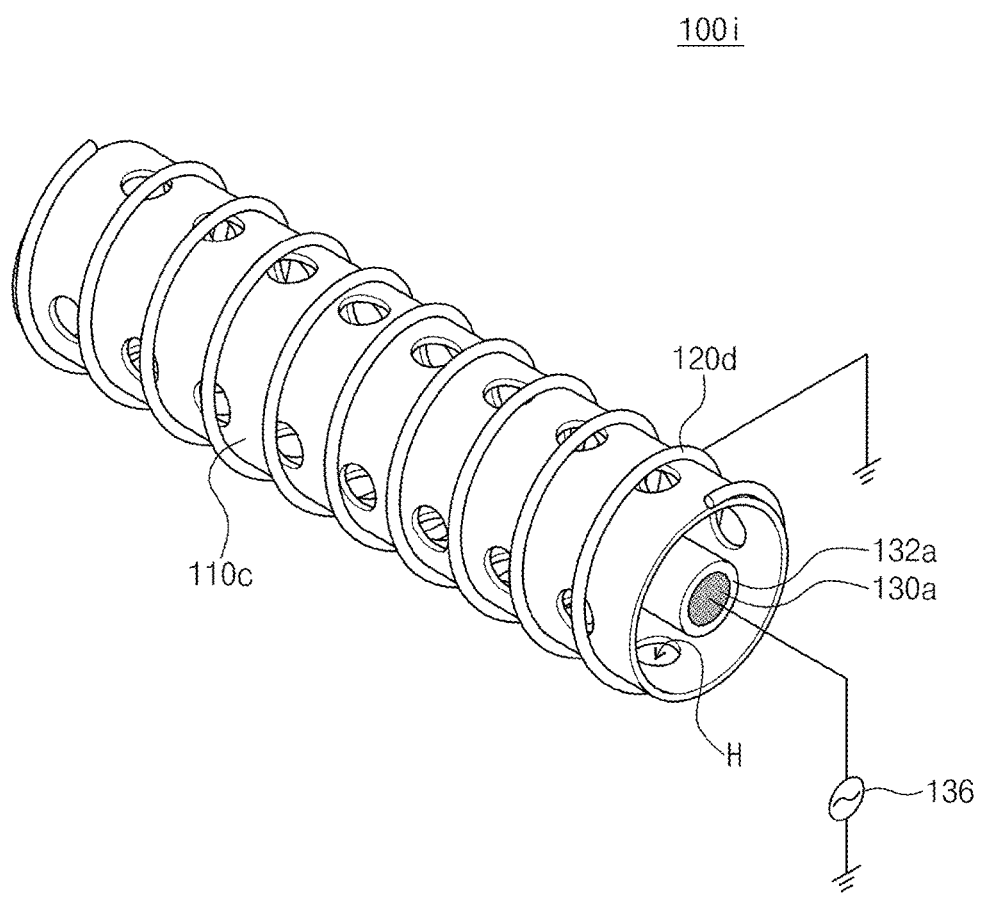
FIGS. 11 and 12 are views respectively illustrating plasma generating apparatuses according to an embodiment of the inventive concept.
Figure 12:
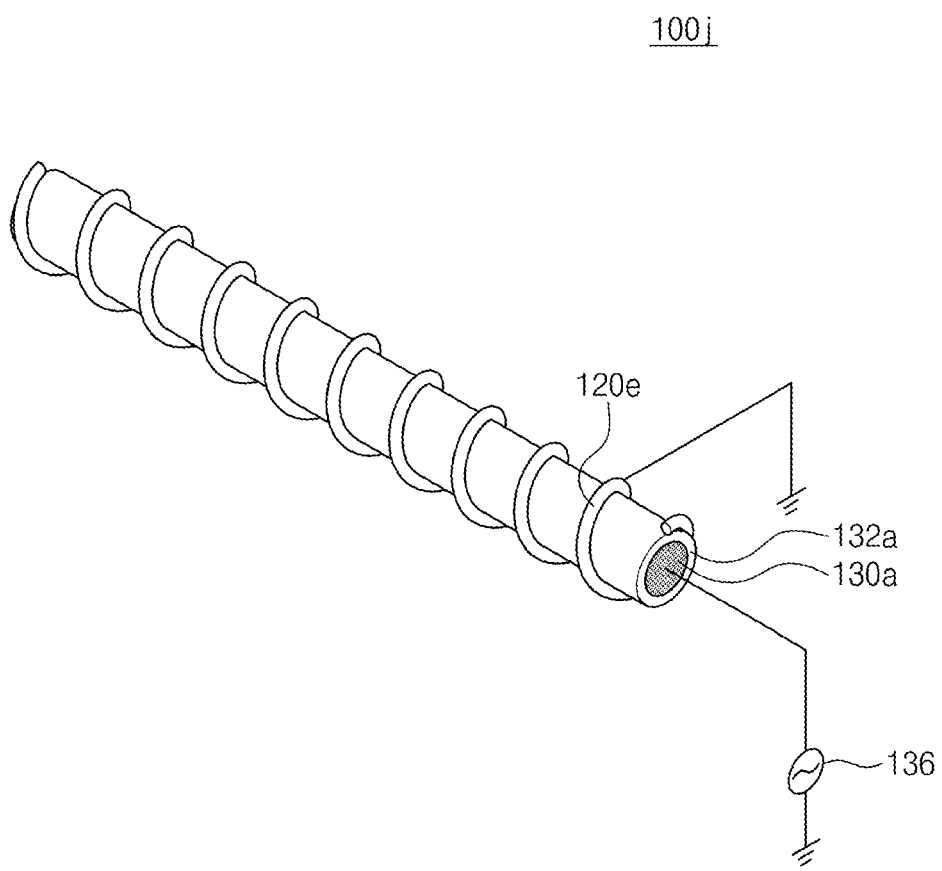

FIGS. 11 and 12 are views respectively illustrating plasma generating apparatuses 100i and 100j according to an embodiment of the inventive concept. The plasma generating apparatus 100i may include a housing 110c, a ground electrode 120d, and a power electrode 130a. The housing 110c may have a cylindrical shape. The power electrode 130a may be provided in the housing 110c, and the ground electrode 120d may surround the housing 110c. The power electrode 130a may include an insulator 132a surrounding the power electrode 130a to prevent filamentary discharge. The process gas is introduced into the housing 110c, and holes H may be defined in a surface of the housing 110c in a direction perpendicular to the introduction direction of the process gas. The generated plasma may be discharged to the outside of the plasma generating apparatus 100i through the holes H. Depending on the number and arrangement of the holes H, large-area plasma may be generated. Although not shown, the ground electrode 120d may further include the insulator. Meanwhile, referring to FIG. 12, the large-area plasma 110j may not include the separated housing. Accordingly, a ground electrode 120e may be directly provided on an insulator 132a of a power electrode 130a. When plasma generation gas is distributed outside the plasma generating apparatus 100j, the plasma generating apparatus 100j may uniformly discharge the plasma gas provided to the outside thereof to generate the large-area plasma. The above-described plasma generating apparatuses 100i and 100j may be used for a bedsore of which an entire area need to be irradiated by the plasma, a human body internal organ, a chamber shaped plasma nozzle using the plasma, formation of uniform plasma of an inside having a space, and atmospheric plasma forming nozzle converting a material in a gas or liquid state or removing biological microorganisms contained to the material.

According to the concept of the present disclosure, provided are the plasma generating apparatuses 100, 100a, 100b, 100c, 100d, 100e, and 100f capable of selectively performing the direct plasma supply and the indirect pre-generated plasma supply to the biological material. Accordingly, the direct method and the indirect method may be selectively used according to the treatment effects and the condition of the target to be treated, and both direct and indirect methods may be used together as necessary. Also, the uniform plasma may be formed over a large area. The plasma generating apparatuses 100, 100a, 100b, 100c, 100d, 100e, and 100f according to an embodiment of the inventive concept may be used for disinfection and care of a skin wound of the biological material, a skin wound and a skin cut caused by a skin disease, a wound inside a human body and abnormal necrosis and cell growth of a cell, and a wound and necrosis of an artificial skin and a human body internal organ.

According to the embodiments of the inventive concept, provided is the plasma generating apparatus capable of selectively performing the direct supply of the plasma or the indirect supply of the pre-generated plasma to the biological material. Accordingly, the direct method and the indirect method may be selectively used according to the treatment effects and the condition of the target to be treated, and both direct and indirect methods may be used together as necessary. Also, the uniform large-area plasma may be formed. The plasma generating apparatus according to the embodiment of the inventive concept may be used for the disinfection and care of the skin wound of the biological material, the skin wound and skin cut caused by the skin disease, the wound inside the human body and the abnormal necrosis and growth of the cell, and the wound and necrosis of the artificial skin and the internal organ in the human body.

As described above, although the plasma generating apparatuses including the housing and the ground electrode, which have various shapes and structures, are exemplarily described, the structures of the housing and ground electrode are not limited thereto. The shape of the electrode may have various structures such as a rod, a surface, and a polygon, and the electrode may be disposed inside and outside the housing. Also, according to an embodiment of the inventive concept, although the ground electrode is exemplarily described to be disposed between the ground electrode and the injection port, an embodiment of the inventive concept is not limited thereto. Selectively, the ground electrode and the power electrode may be exchanged in position. That is, according to the concept of the present disclosure, the scope of the present disclosure may be effective when the direct type and the indirect type plasma generations are compatible.

The description of the present invention is intended to be illustrative, and those with ordinary skill in the technical field of the present invention will be understood that the present invention can be carried out in other specific forms without changing the technical idea or essential features. Therefore, the embodiments described above include exemplary in all respects and not restrictive, but it should be understood.

What is claimed is:

1. A plasma generating apparatus comprising:
    a housing configured to provide an inner space in which plasma is generated;
    a ground electrode coupled to one side of the housing;
    a power electrode coupled to the other side of the housing; and
    a controller configured to control a generation mode of the plasma,
    wherein the generation mode comprises:
    a first mode in which the plasma is provided to a target to be processed while generating the plasma; and
    a second mode in which the plasma is generated in the housing, and then the generated plasma is provided to the target to be processed.

2. The plasma generating apparatus of claim 1, wherein, in the first mode, an electric field formed between the power electrode and the target to be processed is greater than that formed between the power electrode and the ground electrode, and
    in the second mode, the electric field formed between the power electrode and the target to be processed is less than that formed between the power electrode and the ground electrode.

3. The plasma generating apparatus of claim 2, further comprising an adjusting device configured to adjust a distance between the ground electrode and the power electrode, wherein the controller controls the adjusting device.

4. The plasma generating apparatus of claim 3, wherein the controller controls the adjusting device to be positioned between a first position at which a first distance between the power electrode and the target to be processed is less than a second distance between the power electrode and the ground electrode and a second position at which the first distance is greater than the second distance.

5. The plasma generating apparatus of claim 2, wherein the housing comprises:
    an injection port through which a process gas for generating the plasma is injected into the inner space; and
    a discharge port through which the plasma is discharged from the inner space,
    wherein the injection port, the ground electrode, the power electrode, and the discharge port are arranged in a first direction.

6. The plasma generating apparatus of claim 5, wherein, in a cross-section extending in the first direction of the housing, the ground electrode is disposed so that a distance between the ground electrode and the power electrode increases as the ground electrode is away from a surface of the housing.

7. The plasma generating apparatus of claim 5, wherein one portion of the housing, which is disposed adjacent to the injection port, has a first width, and another portion of the housing, which is disposed adjacent to the discharge port, has a second width greater than the first width.

8. The plasma generating apparatus of claim 7, wherein the second width is continuously widened from the first width in the first direction.

9. The plasma generating apparatus of claim 7, wherein the second width is discontinuously widened from the first width in the first direction.

10. The plasma generating apparatus of claim 2, further comprising an ozone removing part configured to remove ozone generated when the plasma is generated.

11. The plasma generating apparatus of claim 10, wherein the ozone removing part comprises:
    a chamber configured to provide a collection space in which the ozone is collected;
    a fan disposed on one side of the chamber to form an inside of the collection space at a low pressure; and
    a filter configured to filter the collected ozone.

12. The plasma generating apparatus of claim 2, further comprising a window disposed on a surface of the housing.

13. A plasma generating apparatus comprising:
a housing configured to provide an inner space in which plasma is generated;
a ground electrode coupled to one side of the housing;
a power electrode coupled to the other side of the housing;
an adjusting device configured to adjust a distance between the ground electrode and the power electrode; and
a controller configured to control the adjusting device,
wherein the controller controls the adjusting device to be positioned between a first position at which a first distance between the power electrode and a target to be processed is less than a second distance between the power electrode and the ground electrode and a second position at which the first distance is greater than the second distance.

14. The plasma generating apparatus of claim 13, wherein the housing comprises:
an injection port through which a process gas for generating the plasma is injected into the inner space; and
a discharge port through which the plasma is discharged from the inner space, and
the ground electrode is disposed between the injection port and the power electrode.

15. The plasma generating apparatus of claim 13, further comprising an ozone removing part configured to remove ozone generated when the plasma is generated.

16. The plasma generating apparatus of claim 15, wherein the ozone removing part comprises:
a chamber configured to provide a collection space in which the ozone is collected;
a fan disposed on one side of the chamber to form an inside of the collection space at a low pressure; and
a filter configured to filter the collected ozone.

17. The plasma generating apparatus of claim 14, wherein one portion of the housing, which is disposed adjacent to the injection port, has a first width, and another portion of the housing, which is disposed adjacent to the discharge port, has a second width greater than the first width.

18. The plasma generating apparatus of claim 14, further comprising a window disposed on a surface of the housing.

* * * * *